United States Patent [19]

Sturm

[11] Patent Number: 5,750,786

[45] Date of Patent: May 12, 1998

[54] PROCESS FOR THE PREPARATION OF UNSUBSTITUTED AND SUBSTITUTED DIARYL PHENYLENEDIAMINES

[75] Inventor: Budd Harvey Sturm, Hartville, Ohio

[73] Assignee: The Goodyear Tire & Rubber Company, Akron, Ohio

[21] Appl. No.: 802,744

[22] Filed: Feb. 20, 1997

[51] Int. Cl.[6] ................................................. C07C 209/18
[52] U.S. Cl. ............................................................. 564/403
[58] Field of Search ........................................... 564/403

[56] References Cited

U.S. PATENT DOCUMENTS

| | | | |
|---|---|---|---|
| 2,824,137 | 2/1958 | Morris | 260/576 |
| 3,081,349 | 3/1963 | Spacht | 260/576 |

*Primary Examiner*—Brian M. Burn
*Attorney, Agent, or Firm*—Bruce J. Hendricks

[57] ABSTRACT

The present invention relates to a process for the preparation of unsubstituted and alkyl-substituted diarylphenylenediamines.

14 Claims, No Drawings

PROCESS FOR THE PREPARATION OF UNSUBSTITUTED AND SUBSTITUTED DIARYL PHENYLENEDIAMINES

BACKGROUND OF THE INVENTION

U.S. Pat. No. 3,432,460 relates to mixtures of ring alkylated diphenyl-para-phenylene diamines and their use in the stabilization of polymers. Such diamines are prepared by reacting in the presence of a condensation catalyst, 1 mol of hydroquinone or ring alkylated hydroquinone with from 2.0 to 2.5 mols of a mixture containing an aryl amines or alkaryl amines. Representative examples of condensation catalysts include metallic halides, phosphoric acid, sulfuric acid, toluene sulfonic acid, alkane sulfonic acid and ammonium chloride.

U.S. Pat. No. 3,081,348 relates to catalysts for condensation reactions of primary amines with dihydroxy aromatic compounds. In particular, this reference teaches the use of amine hydrohalides plus iron compounds as catalysts in a process for condensing primary amines and hydroquinones. The iron compounds may be metallic iron in the form of powders or filings, iron oxides such as FeO, $Fe_2O_3$ and $Fe_3O_4$ and the iron hydroxides.

U.S. Pat. No. 3,081,349 teaches that various metallic halides (such as aluminum chloride, titanium chloride and ferric chloride) are known to catalyze the condensation of various amines and various phenols. Some of the metallic halides produce low yields due to by-product diphenyl amines and tars. Other catalysts of this group catalyze the condensation very slowly at low temperatures and require high temperatures and long reaction times. This reference also teaches reacting a primary amine with dihydroxy aromatic compound in the presence of a liquid hydrocarbon (such as toluene, benzene and xylene) and a catalytic amount of a mixture of free iodine and free iron.

SUMMARY OF THE INVENTION

The present invention relates to a process for the preparation of unsubstituted and alkyl-substituted diarylphenylenediamines.

DETAILED DESCRIPTION OF THE INVENTION

There is disclosed a process for the preparation of aromatic diamines of the formula

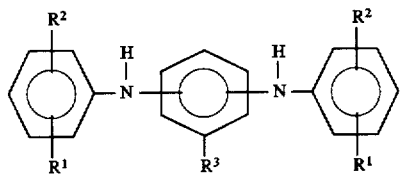

comprising reacting (1) from two to four mols of a primary amine having the following structural formula

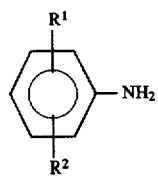

wherein each $R^1$ and $R^2$ are independently selected from the group consisting of hydrogen, alkyl radicals containing from 1 to 20 carbon atoms with (2) one mole of a dihydroxy aromatic compound of the formula

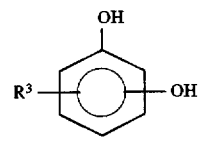

wherein $R^3$ is selected from the group consisting of hydrogen and alkyl radicals having from 1 to 10 carbon atoms, at a temperature of from 175° C. to 350°C. in the presence of a catalytic mixture of (a) from 0.01 to 0.1 mol of a transitional metal halide selected from the group consisting of $TiCl_4$, $AlCl_3$ and mixtures thereof and (b) from 0.001 to 0.1 mol of an iron oxide.

The process of the present invention is useful in the preparation of diaryl phenylenediamines and alkylated diaryl phenylenediamines. Representative of such diamines include N,N'-diphenyl-p-phenylenediamine, N,N'-di-o-tolyl-p-phenylenediamine and N-phenyl-N'-o-tolyl-p-phenylenediamine.

The process of the present invention involves reacting from 2 to 4 mols of a primary amine having the following structural formula:

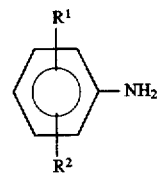

wherein $R^1$ and $R^2$ are selected from the group consisting of hydrogen and alkyl radicals containing from 1 to 20 carbon atoms. Preferably, $R^1$ and $R^2$ are hydrogen or an alkyl radical having 1 carbon atom. Preferably, from 2.1 to 2.8 mols of a primary amine are reacted with every mol of the dihydroxy aromatic compound.

Representative examples of such primary amines include aniline, toluidines (o-m and p), ethyl aniline, propyl aniline, butyl aniline, pentyl aniline, hexyl aniline, heptyl aniline, octyl aniline, nonyl aniline, decyl aniline, dodecyl aniline, xylidine and mixtures of such primary amines.

The above primary amines are reacted with a dihydroxy aromatic compound of the formula

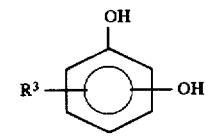

wherein $R^3$ is selected from the group consisting of hydrogen and alkyl radicals having from 1 to 10 carbon atoms. Preferably, $R^3$ is hydrogen or an alkyl radical having 1 carbon atom.

Representative examples of such dihydroxy compounds include hydroquinone, resorcinol and catechol.

The reaction is conducted at a temperature ranging from 175° C. to 350° C. Preferably, the reaction is conducted at a temperature ranging from about 200° to 300° C.

The reaction is conducted in the presence of a catalytic mixture containing from 0.01 to 0.1 mol of a transitional metal halide per mole of the dihydroxy aromatic compound of formula III. Representative examples of such transitional metal halides include $TiCl_4$, $AlCl_3$ and mixtures thereof. Preferably, the transitional metal halide is $TiCl_4$. The preferred amount of transitional metal halide is from 0.02 to 0.05 mols per mole of dihydroxy compound.

The catalytic mixture also contains from 0.001 to 0.1 mol of an iron oxide per mole of the dihydroxy aromatic compound of formula III. Preferably, the catalytic mixtures contain from 0.01 to 0.05 mol of an iron oxide. Representative examples of suitable iron oxides include FeO, $Fe_2O_3$, $Fe_3O_4$ and mixtures thereof. Preferably, the iron oxide is $Fe_2O_3$ and mixtures of $Fe_2O_3$ and $Fe_3O_4$.

The reaction may be conducted in the presence of a solvent capable of forming an azeotrope with water. These compounds may be well known liquid hydrocarbons such as toluene, benzene, xylene and mixtures thereof.

The invention is further characterized by the following examples which are not intended to be intended as limitations on the scope of the invention.

EXAMPLE 1

A series of controls and examples were conducted to compare and contrast the various aspects of the present invention. In particular, a series of controls where conducted using transitional metal halides as the sole catalyst in the condensation reaction. In addition, there was conducted condensation reactions where both a transitional metal halide and iron oxide was used as co-catalysts. In each reaction, 1 mole of hydroquinone was reacted with 1.25 mols of aniline and 1.25 mols of o-toluidine.

The reaction was conducted in a 1-liter flask equipped with a heating mantle, stirrer, dropping funnel, thermometer and a vacuum jacketed packed column topped by a Dean-Stark trap with an overhead thermometer and water condenser. To the flask was charged 110 grams of hydroquinone (1 mol), 46.4 grams of aniline (0.5 mol), 53.6 grams of o-toluidine (0.5 mol) and the catalyst (control or catalyst mixture). Forty weight percent (100.0 grams) of the amines were initially charged so that a high reaction temperature can be maintained in the pot without flooding the packed column with excess unreacted amines. Ten grams of xylene was added and the reaction stirred with heating to 240° C. The remaining amines (150 grams consisting of 69.6 grams of aniline and 80.4 grams of o-toluidine) were slowly added dropwise while maintaining the pot temperature at 235°–265° C. A total of 116 grams of aniline (1.25 mol) and 134 grams (1.25 mol) of o-toluidine were added. The water was removed from the Dean-Stark trap over the reaction period until the rate was less than 1 ml per hour. The amount of water was used to determine the degree of completion of the reaction. The catalyst(s) were neutralized with aqueous sodium carbonate at 90°–95° C. The reaction mixture was stripped to 275°–285° C. at 20–40 mm pressure. The level of the three major products, (N,N'-di-o-tolyl-p-phenylenediamine), (N,N'-diphenyl-p-phenylenediamine) and (N-phenyl-N'-o-tolyl-p-phenylenediamine), were determined by gas chromatograph.

Table 1 below provides the grams of catalyst used, the weight percent of (N,N'-diphenyl-p-phenylenediamine), identified as DPPD, (N,N'-di-o-tolyl-p-phenylenediamine), identified DTPD and (N-phenyl-N'-o-tolyl-p-phenylenediamine), identified PTPD.

TABLE 1

|  | Control Sample 1 | Control[1] Sample 2 | Control Sample 3 | Sample 4 | Sample 5 | Sample 6 | Control[2] Sample 7 | Sample 8 |
|---|---|---|---|---|---|---|---|---|
| Catalyst mol (grams) | 0.3 (5.0) $FeCl_3$ | .03 (5.0) $FeCl_3$ | .03 (5.6) $TiCl_4$ | .02 (3.65) $TiCl_4$ | .025 (4.8) $TiCl_4$ | .033 (6.2) $TiCl_4$ | .038 (5.0) $AlCl_3$ | .038 (5.0) $AlCl_3$ |
| Catalyst mol (grams) |  | .016 (2.5) $Fe_2O_3$ |  | .016 (2.5) $Fe_2O_3$ | 0.16 (2.5) $Fe_2O_3$ | .016 (2.5) $Fe_2O_3$ |  | .016 (2.5) $Fe_2O_3$ |
| % by wgt DPPD | 20.2 |  | 18.1 | 18.6 | 21.1 | 22.3 |  | 21.2 |
| % by wgt DTPD | 42.8 |  | 37.9 | 42.8 | 42.8 | 45.0 |  | 42.2 |
| % by wgt PTPD | 20.5 |  | 19.4 | 20.9 | 21.3 | 20.8 |  | 20.1 |
| % by wgt DPPD + DTPD + PTPD | 83.5 |  | 75.4 | 82.3 | 85.2 | 88.1 |  | 83.5 |
| Reaction Time (hrs) | 4.0 | 5.0 | 4.5 | 1.0 | 1.8 | 1.5 | 4.0 | 2.5 |
| % Crude Yield | 95.6 |  | 94.0 | 92.7 | 96.2 | 96.9 |  | 94.8 |

[1]Analysis not conducted because reaction not completed (95% completion)
[2]Analysis not conducted because reaction not completed (83% completion)

As can be seen from the data in Table 1, Control Sample 1 required 4 hours of reaction time. Control Sample 2 was an incomplete reaction after 5 hours. Similarly, Control Sample 3 required 4½ hours to complete the reaction. Samples 4, 5, 6 and 8 required significantly less reaction times with acceptable yields of desired product. Control 7 was similar to the other controls in the reaction time required.

EXAMPLE 2

The procedure used in Example 1 was repeated with a number of catalyst combinations which are listed below in Table 2.

TABLE 2

| CONTROLS | | | | |
|---|---|---|---|---|
|  | Catalyst mol (g) | $Fe_2O_3$ mol (g) | Reaction Time (hrs) | % Completion |
| Sample 1 | .05 (5.0) $H_3PO_4$ | .016 (2.5) | 5.0 | 74 |

TABLE 2-continued

CONTROLS

| | Catalyst mol (g) | Fe$_2$O$_3$ mol (g) | Reaction Time (hrs) | % Completion |
|---|---|---|---|---|
| Sample 2 | .03 (5.0) FeCl$_3$ | .016 (2.5) | 5.0 | 95 |
| Sample 3 | .02 (5.5) SnCl$_4$ | .016 (2.5) | 5.0 | 81 |
| Sample 4 | .028 (5.4) VCl$_4$ | .016 (2.5) | 5.5 | 82 |
| Sample 5 | .018 (5.0) MoCl$_5$ | .016 (2.5) | 4.0 | 100 |
| Sample 6 | 0.2 (5.0) ZrCl$_4$ | .016 (2.5) | 5.0 | 100 |
| Sample 7 | .032 (5.0) CrCl$_3$ | .016 (2.5) | 6.0 | 92 |
| Sample 8 | .013 (5.0) WCl$_6$ | .016 (2.5) | 5.0 | 94 |
| Sample 9 | .046 (6.25) ZnCl$_2$ | .016 (2.5) | 5.0 | 67 |
| Sample 10 | .048 (6.25) NiCl$_2$ | .016 (2.5) | 5.0 | 83 |
| Sample 11 | .046 (6.25) CuCl$_2$ | .016 (2.5) | 6.0 | 88 |
| Sample 12 | .05 (6.25) MnCl$_2$ | .016 (2.5) | 5.0 | 72 |
| Sample 13 | .048 (6.25) CoCl$_2$ | .016 (2.5) | 5.0 | 69 |
| Sample 14 | .126 (12.5) CuCl | .016 (2.5) | 3.5 | 91 |
| Sample 15 | .031 (8.0) SnCl$_2$ | .016 (2.5) | 6.0 | 67 |

As can be seen from the relative completions, none of the control samples catalysts provided for a completed reaction or required reaction times of four hours or more (Samples 5 and 6).

What is claimed is:

1. A process for the preparation of aromatic diamines of the formula

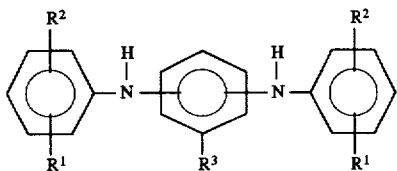    I comprising reacting (1) from two to four mols of a primary amine having the following structural formula

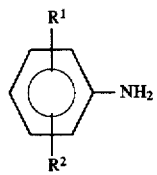    II wherein each R$^1$ and R$^2$ are independently selected from the group consisting of hydrogen, alkyl radicals containing from 1 to 20 carbon atoms with (2) one mole of a dihydroxy aromatic compound of the formula

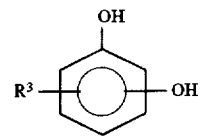    III wherein R$^3$ is selected from the group consisting of hydrogen and alkyl radicals having from 1 to 10 carbon atoms, at a temperature of from 175° C. to 350°C. in the presence of a catalytic mixture of (a) from 0.01 to 0.1 mol of a transitional metal halide selected from the group consisting of TiCl$_4$, AlCl$_3$ and mixtures thereof and (b) from 0.001 to 0.1 mol of an iron oxide.

2. The process of claim 1 wherein each R$^1$ and R$^2$ are hydrogen.

3. The process of claim 1 wherein each R$^1$ is an alkyl radical containing 1 carbon atom and each R$^2$ is hydrogen.

4. The process of claim 1 wherein R$^3$ is hydrogen.

5. The process of claim 1 wherein a mixture of two or more primary amines of formula II are reacted with a dihydroxy aromatic compound of formula III.

6. The process of claim 5 wherein said mixture of two or more primary amines, one of the primary amines is characterized by R$^1$ and R$^2$ are both hydrogen and said second primary amine is characterized by R$^1$ is an alkyl radical containing 1 carbon atom and R$^2$ is hydrogen.

7. The process of claim 1 wherein the reaction of the primary amine with the dihydroxy aromatic compound is conducted in the presence of a liquid hydrocarbon capable of forming an azeotrope with water.

8. The process of claim 7 wherein said liquid hydrocarbon is selected from the group consisting of toluene, benzene, xylene and mixtures thereof.

9. The process of claim 1 wherein said catalytic mixture comprises from 0.02 to 0.05 mol of said transitional metal halide and from 0.01 to 0.05 mol of said iron oxide.

10. The process of claim 1 wherein said transitional metal halide is TiCl$_4$.

11. The process of claim 1 wherein said transitional metal is AlCl$_3$.

12. The process of claim 1 wherein said iron oxide is selected from the group consisting of FeO, Fe$_2$O$_3$, Fe$_3$O$_4$ and mixtures thereof.

13. The process of claim 12 wherein said iron oxide is Fe$_2$O$_3$.

14. The process of claim 12 wherein said iron oxide is a mixture of Fe$_2$O$_3$ and Fe$_3$O$_4$.

* * * * *